United States Patent [19]

Schiller

[11] Patent Number: 5,733,881

[45] Date of Patent: Mar. 31, 1998

[54] OPIOID PEPTIDE ANTAGONISTS

[75] Inventor: Peter Schiller, Montreal, Canada

[73] Assignee: Astra AB, Sweden

[21] Appl. No.: 507,370

[22] PCT Filed: Jun. 14, 1995

[86] PCT No.: PCT/SE95/00721

§ 371 Date: Aug. 22, 1995

§ 102(e) Date: Aug. 22, 1995

[87] PCT Pub. No.: WO95/35316

PCT Pub. Date: Dec. 28, 1995

[30] Foreign Application Priority Data

Jun. 20, 1994 [SE] Sweden .................................. 9402170
Aug. 25, 1994 [SE] Sweden .................................. 9402838

[51] Int. Cl.$^6$ .............................. A61K 38/00; C07K 5/00; C07K 7/00; C07K 17/00
[52] U.S. Cl. ........................... 514/18; 514/19; 514/885; 514/886; 530/330; 530/331; 530/302; 530/333; 530/334; 530/335; 530/336; 530/337; 530/338
[58] Field of Search ........................ 530/330, 331, 530/302, 333–338; 514/18–19, 885, 886

[56] References Cited

FOREIGN PATENT DOCUMENTS

WO 94/15959   7/1994   WIPO .

OTHER PUBLICATIONS

Temussi et al. BBRC vol. 198 p. 933, Feb. 1994.
Merck. 11th edition pp. 1006–1007, 1989.
Cotton et al., "ICI 174864: A Highly Selective Antagonist for the Opioid δ–Receptor," *Eur. J. Pharmacol.* 97:331–332 (1984).
Portoghese et al., "Application of the Message-Address Concept in the Design of Highly Potent and Selective Non-Peptide δ Opioid Receptor Antagonists," *J. Med. Chem.* 31:281–282 (1988).
Portoghese, "An Approach to the Design of Receptor-Type-Selective Non-Peptide Antagonists of Peptidergic Receptors: δ Opioid Antagonists," *J. Med. Chem.* 34:1757–1762 (1991).

Schiller et al., "A New Class of Potent and Highly Selective δ Opioid Receptor Peptide Antagonists Without μ Antagonist Properties," *FASEB J.* 6:A1575, Abstract No. 3699 (1992).

Schiller et al., "Differential Stereochemical Requirements of μ vs. δ Opioid Receptors for Ligand Binding and Signal Transduction: Development of a Class of Potent and Highly δ–Selective Peptide Antagonists," *Proc. Natl. Acad. Sci. USA* 89:11871–11875 (1992).

Schiller et al., "TIPP[ψ]: A Highly Potent and Stable Pseudopeptide δ Opioid Receptor Antagonist with Extraordinary δ Selectivity," *J. Med. Chem.* 36:3182–3187 (1993).

*Primary Examiner*—Sheela Huff
*Attorney, Agent, or Firm*—Michael A. Sanzo; Vinson & Elkins

[57] ABSTRACT

Compounds of the formula I as well as methods for their preparation, their pharmaceutical preparations and their use.

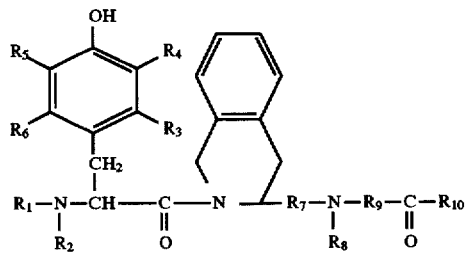

The compounds of formula I are useful in therapy, especially as analgesics and as immunosuppresive agents.

15 Claims, No Drawings

OPIOID PEPTIDE ANTAGONISTS

THE FIELD OF THE INVENTION

This invention is related to a new class of opioid peptide analogs that are δ opioid receptor antagonists as well as to their synthesis and their use as analgesic and immunosuppressive compounds.

BACKGROUND AND PRIOR ART

A known nonpeptide δ opioid antagonist is naltrindole, which is described by P. S. Portoghese, et al J. Med. Chem. 31, 281–282 (1988). Naltrindole has similar δ antagonist potency as the compounds according to this invention but is much less δ selective. Furthermore, naltrindole has also quite high μ opioid receptor affinity ($K_i^\mu$=12 nM) in the receptor binding assay and potent μ antagonist properties ($K_e$=29 nM) in the guinea pig ileum (GPI) assay, cf P. S. Portoghese, J. Med. Chem. 34, 1757–1762 (1991).

Another known δ-antagonist is the enkephalin analog (ICI 174864) described by R. Cotton, et al. in Eur. J. Pharmacol. 97, 331–332 (1984). In comparison with the δ antagonists described in this patent application, ICI 174864 is much less δ-selective (10–300 times less) and has much lower antagonist potency in the MVD assay (40–1000 times less potent).

Peptides containing the H-Tyr-Tic-Aaa-sequence (Tic=1,2,3,4-tetrahydroisoquinoline-3-carboxylic acid, Aaa= aromatic amino acid residue) at the N-terminus and which are very potent and highly selective δ antagonists have recently been disclosed by P. W. Schiller et al. in FASEB J, 6 (No. 4), A1575 (1992), at the International Narcotics Research (INRC) Meetings in Keystone, Colo., Jun. 24–29 (1992) and in Skövde, Sweden, Jul. 10–15 (1993), at the 2nd Japan Symposium on Peptide Chemistry Shi-zuoka, Japan, Nov. 9–13 (1992), at the 22nd European Peptide Symposium, Interlaken, Switzerland, Sep. 13–19 (1992), in Proc. Natl. Acad. Sci. U.S.A. 89, 11871–11875 (1992), and in J. Med. Chem. 36, 3182–3187 (1993).

Thus, the problem underlying the present invention was to find δ opioid antagonists both with high δ antagonist potency and with high δ selectivity.

THE INVENTION

It has now been found that peptides containing the H-Tyr-Tic-dipeptide segment at the N-terminus and a non-aromatic amino acid residue at the 3-position of the peptide sequence, as defined by the following formula I, have extraordinary potency as δ antagonists high selectivity for the δ receptor total lack of μ antagonist properties.

The compounds according to the present invention have the general formula I

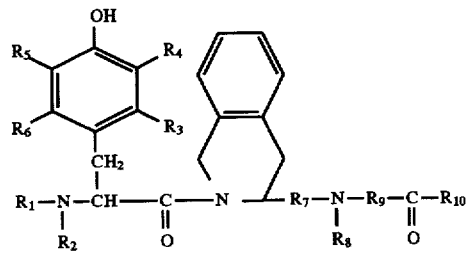

wherein $R_1$ is H; $CH_3(CH_2)_n$— wherein n=0–12;

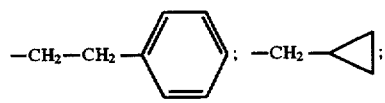

—$CH_2$—$CH$=$CH_2$; or arginine;

$R_2$ is H; $CH_3(CH_2)_n$— wherein n=0–12; $CH_3$—;

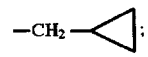

or

—$CH_2$—$CH$=$CH_2$;

$R_3$, $R_4$, $R_5$ and $R_6$ are all H; or $R_4$ and $R_5$ are both H and $R_3$ and $R_6$ is each a $C_1$–$C_6$ alkyl group; or $R_3$, $R_5$ and $R_6$ are all H and $R_4$ is F, Cl, Br, I, OH, $NH_2$ or $NO_2$;

$R_7$ is C=O or $CH_2$;

$R_8$ is H or a $C_1$–$C_6$ alkyl group;

$R_9$ is selected from

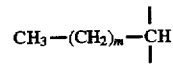

wherein m is 0–12;

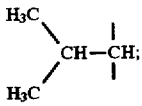

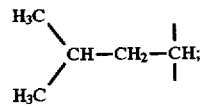

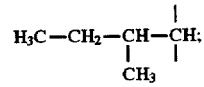

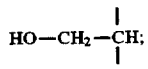

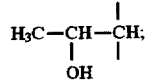

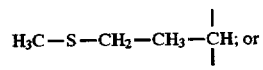

wherein p is 0–4;

$R_{10}$ is OH, $NH_2$ or

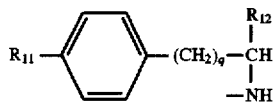

wherein $R_{11}$ is H, $NO_2$, F, Cl, Br or I; q is 0–3;
$R_{12}$ is COOH, $CONH_2$, $CH_2OH$, or any additional amino acid or peptide segment; or $R_{10}$ is

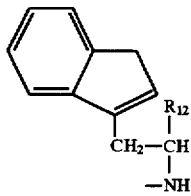

wherein $R_{12}$ is as defined above.

Preferred compounds of the invention are those compounds wherein $R_1$ is selected from H or $CH_3$;
$R_2$ is selected from H or $CH_3$;
$R_3$ is selected from H or $CH_3$;
$R_4$ is H;
$R_5$ is H;
$R_6$ is selected from H or $CH_3$;
$R_7$ is selected from CO or $CH_2$;
$R_8$ is selected from H or $CH_3$;
$R_9$ is selected from

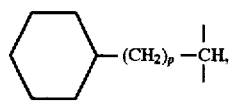

wherein p=0–4 or

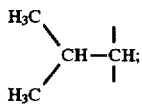

$R_{10}$ is selected from

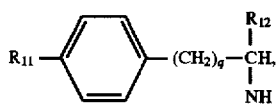

wherein $R_{11}$ is H, $NO_2$, F, Cl, Br or I,
q is 1–3, and $R_{12}$ is COOH.

Especially preferred compounds of the invention are those compounds wherein $R_1$ is selected from H or $CH_3$;
$R_2$ is selected from H or $CH_3$;
$R_3$ is selected from $CH_3$;
$R_4$ is selected from H;
$R_5$ is selected from H;
$R_6$ is selected from $CH_3$;
$R_7$ is selected from $CH_2$;
$R_8$ is selected from H or $CH_3$;

$R_9$ is selected from

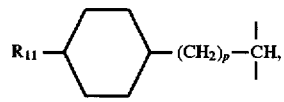

wherein p=0–4;
$R_{10}$ is selected from

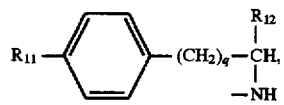

wherein $R_{11}$ is H, q is 1, and $R_{12}$ is COOH.

Especially preferred compounds according to the invention are those wherein $R_9$ is

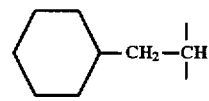

(containing a cyclohexylalanine [Cha] residue in the 3-position of the peptide sequence). Substitution of Cha in the 3-position significantly enhances δ antagonist potency.

Further preferred compounds according to the invention are those, wherein $R_4$ and $R_5$ are hydrogen and $R_3$ and $R_6$ are both methyl groups.

Also preferred compounds according to the invention are compounds wherein $R_7$ is a part of a reduced peptide bond.

The best mode of carrying out the invention known at present is to use the compounds of Examples 1, 2, 5, 11, 12 and 15.

SYNTHESIS

Most Boc-amino acid derivatives used in the peptide syntheses are commercially available. 2,6-dimethyl-tyrosine (Dmt) was prepared as described by J. H. Dygos et al. Synthesis, No 8 (August) pp. 741–743 (1992).

All peptides were prepared by solid-phase techniques. The usual polystyrene/-divinylbenzene resin was used for the solid-phase synthesis of peptides with a free C-terminal carboxyl group, whereas peptide amides were synthesized by using the p-methylbenzhydrylamine resin. Boc protection of the amino group was employed in the preparation of all peptides. The syntheses were performed according to protocols that have been extensively used in the inventor's laboratory (P. W. Schiller et al, Biochemisty 16, 1831–1832 (1977)). Couplings were performed in $CH_2Cl_2$, DMF or a mixture thereof, using N,N'-dicyclohexylcarbodiimide/1-hydroxybenzotriazole (DCC/HOBt), N,N'-diisopropylcarbodiimide/1-hydroxybenzotriazole, benzotriazolyloxytris-(dimethylamino)phosphonium hexafluorophosphate, or any other suitable coupling agent. Completeness of coupling was carefully examined after each coupling step by means of the ninhydrin color test. The fully assembled peptide chain was cleaved from the resin and completely deprotected by treatment with liquid HF at 0° C. and in the presence of anisole as scavenger (60–90 min).

Crude products obtained from solid-phase peptide synthesis required extensive purification by various chromatographic techniques or by other methods. Following HF cleavage and extraction of the resin, gel filtration on Sephadex (G-15 or G-25) was routinely performed. Various subsequent purification steps included partition chromatography on Sephadex G-25 (using various butanol-acetic acid-pyridine-water two phase systems), ion exchange chromatography (DEAE-Sephadex, SP-Sephadex and CM-cellulose) and reversed-phase chromatography on an octadecasilyl-silica column using linear gradients of methanol in 1% trifluoroacetic acid (low pressure). If necessary, final purification to homogeneity was performed by semi-preparative HPLC. Semi-preparative μ-Bondapak C-18 columns (Waters; 0.7×25 cm), which, depending on the separation problem, permitted purification of 2–20 mg peptide material per run were used. Several highly sensitive and efficient analytical methods were used to demonstrate homogeneity of the prepared peptides and to verify their structures. Thin layer chromatography in at least two different solvent systems was used to establish purity. Furthermore, analytical HPLC in two or three different solvent systems was routinely used in the laboratory as a highly sensitive purity test. Verification of peptide structures was mainly based on amino acid analysis and fast atom bombardment-mass spectrometry (FAB-MS). For amino acid analyses, peptides were hydrolyzed in 6N HCl containing a small amount of phenol for 24 h at 110° C. in deaerated tubes (in some case hydrolyses lasting for 12 and 48 h were also performed to take into account amino acid degradation). Hydrolysates were analyzed on a Beckman Model 121 C amino acid analyzer equipped with a system AA computing integrator. FAB mass spectrometry was used to establish the correct molecular weights of the peptides.

DETAILED DESCRIPTION OF THE INVENTION

The invention will now be described in more detail by the following examples.

EXAMPLE 1

Preparation of H-Tyr-Tic-Cha-Phe-OH (SEQ ID NO:1)

Boc-Phe-O-resin (1 g, 0.61 mmol Boc-Phe/g resin; Peninsula, Belmont, Calif.) was washed with reagents in the following sequence: $CH_2Cl_2$ (3×1 min), 50% (v/v) TFA in $CH_2Cl_2$ (30 min), $CH_2Cl_2$ (5×1 min), 10% (v/v) DIEA in $CH_2Cl_2$ (2×5 min), $CH_2Cl_2$ (5×1 min). Boc-Cha-OH (412 mg, 1.52 mmol) was then coupled using HOBt (205 mg, 1.52 mmol) and DCC (313 mg, 1.52 mmol) in $CH_2Cl_2$/DMF (3:1, v/v) for 17 h. The resin was then washed with $CH_2Cl_2$ (3×1 min), EtOH (1 min), $CH_2Cl_2$ (3×1 min). This sequence of washes and reactions was repeated for the addition of each of the residues with the following modifications.

After coupling of Boc-Tic-OH the resin was washed with $CH_2Cl_2$/DMF (3:1, v/v) (3x) and a recoupling step using the same amounts of Boc-Tic-OH, HOBt and DCC in $CH_2Cl_2$/DMF (3:1, v/v) was performed for another 17 h. The same recoupling step was also carried out to couple Boc-Tyr(Boc)-OH: After final deprotection with 50% (v/v) TFA in $CH_2Cl_2$ (30 min), the resin was washed with $CH_2Cl_2$ (3×1 min) and EtOH (3×1 min) and was dried in a desiccator. The dry resin was treated with 20 ml of HF plus 1 ml of anisole (per gram of resin) first for 90 min at 0° C. and then for 15 min at room temperature. After evaporation of the HF, the resin was extracted three times with $Et_2O$ and, subsequently three times with 7% AcOH. The crude peptide was then obtained in solid form through lyophilization of the combined acetic acid extracts.

The peptide was purified by gel filtration on a Sephadex-G-25 column in 0.5 N AcOH followed by reversed-phase chromatography on an octadecasilyl silica column with a linear gradient of 0–80% MeOH in 1% TFA. After solvent evaporation the pure peptide was dissolved in conc. AcOH and was obtained in solid form through lyophilization. Yield: 45 mg FAB—MS:MH$^+$=640

| TLC (silica) | Rf0.75 n-BuOH/AcOH/H$_2$O (4/1/5, organic phase) Rf0.70 n-BuOH/Pyridine/AcOH/H$_2$O (15/10/3/12) |
|---|---|

Amino acid analysis: Tyr 0.96, Phe 1.00

EXAMPLE 2

Preparation of H-Tyr-TicΨ[CH$_2$—NH]Cha-Phe-OH (SEQ ID NO:2)

The synthesis of this peptide was performed as in the case of EXAMPLE 1 using the same resin except that the introduction of a reduced peptide bond between the Tic$^2$ and Cha residue required a reductive alkylation reaction between Boc-Tic aldehyde and the amino group of the resin-bound H-Cha-Phe dipeptide.

Preparation of N-t-butoxycarbonyl-L-1,2,3,4-tetrahydroisoquinoline-3-aldehyde (Boc-Tic Aldehyde) Via N-t-butoxycarbonyl-L-1,2,3,4-tetrahydroisocluinoline-3-N-methoxy, N-methylamide BOP (benzotriazol-1-yl-oxytris(dimethylamino) phosphonium hexafluorophosphate) (3.48 g, 10 mmol) was added to a stirred solution of Boc-Tic-OH (2.8 g, 10 mmol) and triethylamine (1.33 ml, 10 mmool) in $CH_2Cl_2$. After five minutes, N-dimethylhydroxylamine hydrochloride (1.2 g, 12 mmol) and triethylamine (1.68 ml, 12 mmol) were added to the solution. The reaction was carried out for 17 h. Subsequently, the reaction mixture was diluted with dichloromethane and washed with 3N HCl, a saturated aqueous solution of NaHCO$_3$ and a saturated aqueous solution of NaCl. The organic solution was dried over MgSO$_4$ prior to evaporation of the solvent. The resulting crude product of N-t-butoxycarbonyl-L-1,2,3,4-tetrahydroisequinoline-3-N-methoxy, N-methylamide was purified by chromatography on a silica gel column in EtOAc/hexane(1:2, v/v). Yield: 2.1 g (65%), oil

| TLC (silica) | Rf0.57 EtOAc/hexane (1/1) Rf0.30 EtOAc/hexane (1/2) |
|---|---|

NMR (CDCl$_3$) δ1.45 (9H,t-butyl), 3.00 (2H,H-4), 3.18 (3H, NCH$_3$), 3.8(3H, OCH$_3$), 4.42–4.90(3H, 2H-1 and 1H-3), 7.17(4H, ar)

To a stirred solution of N-t-butoxycarbonyl-L-1,2,3,4-tetrahydroisoquinoline-3-N-methoxy, N-methylamide (1.2 g, 4 mmol) in 30 ml ether 190 mg (5 mmol) of lithium aluminium hydride were added. The reduction reaction was carried out for 1 h and the reaction mixture was then hydrolyzed with a solution of KHSO$_4$ (954 mg, 7 mmol) in water (20 ml). Subsequently, the aqueous phase was separated and extracted with three 50 ml portions of ether. The four organic phases were combined, washed with 3 N HCl, a saturated aqueous solution of NaHCO$_3$ and a saturated aqueous solution of NaCl, and finally dried over MgSO$_4$. After solvent evaporation the aldehyde was obtained in pure form as an oil. Yield: 635 mg (60%), oil NMR(CDCl$_3$) δ1.5 (9H, t-butyl), 3.0–3.27 (2H, H-4), 4.4–4.8 (3H, 1H-3 and 2H-1), 7.0–7.2 (4H, ar), 9,43 (1H, CHO)

TLC (silica)  Rf0.84 EtOAc/hexane (1/1)
              Rf0.57 EtOAc/hexane (1/2)

Reductive Alkylation Reaction Between Boc-Tic Aldehyde and the H-Cha-Phe-O Resin The resin was washed with DMF (2×1 min) and then Boc-Tic aldehyde (392 mg, 1.52 mmol) in DMF containing 1% AcOH was added to the resin. Sodium cyanoborohydride (115 mg, 1.83 mmol) was then added portionwise over a period of 40 min and the reaction was allowed to continue for 3h.

After coupling of the N-terminal tyrosine residue and deprotection the peptide was cleaved from the resin, purified and lyophilized as described in EXAMPLE 1. Yield: 285 mg FAB—MS: MH$^+$=627

TLC (silica)  Rf0.73 n-BuOH/AcOH/H$_2$O (4/1/5, organic phase)
              Rf0.85 n-BuOH/pyridine/AcOH/H$_2$O (15/10/3/12)

The compounds of Examples 3–14 have been synthesized as described for Example 1 above, and the compound of Example 15 was synthesized as described for Example 2 above.

The compounds in Table 1 according to the invention have been synthesized and tested as δ antagonists.

TABLE 1

| Ex. | Compound | FAB—MS MH$^+$ (molecular weight) |
|---|---|---|
| 1 | H—Tyr—Tic—Cha—Phe—OH (SEQ ID NO:1) | 641 |
| 2 | H—Tyr—Ticψ[CH$_2$—NH]Cha—Phe—OH (SEQ ID NO:2) | 627 |
| 3 | H—Tyr—Tic—Cha—Phe—NH$_2$ (SEQ ID NO:3) | 640 |
| 4 | H—Tyr—Tic—Leu—Phe—OH (SEQ ID NO:4) | 601 |
| 5 | H—Tyr—Tic—Val—Phe—OH (SEQ ID NO:5) | 587 |
| 6 | H—Tyr—Tic—Nva—Phe—OH (SEQ ID NO:6) | 587 |
| 7 | H—Tyr—Tic—Nle—Phe—OH (SEQ ID NO:7) | 601 |
| 8 | H—Tyr—Tic—Ile—Phe—OH (SEQ ID NO:8) | 601 |
| 9 | H—Tyr—Tic—Thr—Phe—OH (SEQ ID NO:9) | 589 |
| 10 | H—Tyr—Tic—Met—Phe—OH (SEQ ID NO:10) | 619 |
| 11 | H—Dmt—Tic—Cha—Phe—OH (SEQ ID NO:11) | 669 |
| 12 | H—D—Dmt—Tic—Cha—Phe—OH (SEQ ID NO:12) | 669 |
| 13 | H—Dmt—Tic—Cha—Phe—NH$_2$ (SEQ ID NO:13) | 668 |
| 14 | H—Tyr(3'-I)—Tic—Cha—Phe—OH (SEQ ID NO:14) | 767 |
| 15 | H—Dmt—Ticψ[CH$_2$—NH]Cha—Phe—OH (SEQ ID NO:15) | 655 |

Pharmacological Testing in Vitro of δ Opioid Antagonists

Biosassys based on inhibition of electrically evoked contractions of the mouse vas deferens (MVD) and of the guinea pig ileum (GPI) were made. In the GPI assay the opioid effect is primarily mediated by μ opioid receptors, whereas in the MVD assay the inhibition of the contractions is mostly due to interaction with δ opioid receptors. Antagonist potencies in these assays are expressed as so-called K$_e$-values (H. W. Kosterlitz & A. J. Watt, Br. J. Pharmacol. 33, 266–276 (1968)). Agonist potencies are expressed as IC$_{50}$ values (concentration of the agonist that produces 50% inhibition of the electrically induced contractions).

Bioassays Using Isolated Organ Preparations

The GPI and MVD bioassays were carried out as reported in P. W. Schiller et at., Biochem. Biophys. Res. Commun 85, 1332–1338 (1978) and J. Di Maio et al., J. Med. Chem. 25, 1432–1438 (1982). A log dose-response curve was determined with [Leu$^5$]enkephalin as standard for each ileum and vas preparation, and IC$_{50}$ values of the compounds being tested were normalized according to A. A. Waterfield et al., Eur. J. Pharmacol. 58, 11–18 (1979). K$_e$ values for the δ opioid antagonists were determined from the ratio of IC$_{50}$ values (DR) obtained in the presence and absence of a fixed antagonist concentration (a) (K$_e$=a/(DR-1)) H. W. Kosterlitz & A. J. Watt, Br. J. Pharmacol. 33, 266–276 (1968). These determinations were made with the MVD assay, using two different δ-selective agonists DPDPE and [D-Ala$^2$] deltorphin I.

Conclusion

All compounds show high δ antagonist properties.

Peptides containing a cyclohexylalanine (Cha) residue in the 3-position of the peptide sequence are more potent δ antagonists than corresponding peptides with an aromatic amino acid in position 3.

All compounds showed no μ antagonist activity in the GPI assay at concentrations as high as 10 μM.

In the GPI assay most compounds showed very weak partial μ agonist activity (maximal inhibition of electrically evoked contractions ranging from 20% to 53%)

Opioid Receptor Binding Assays

μ and δ opioid receptor binding constants (K$_i^μ$, K$_i^δ$) of the compounds were determined by displacement of relatively selective μ and δ radioligands from binding sites in rat brain membrane preparations (calculated from the measured IC$_{50}$ values on the basis of the equation by Cheng & Prusoff (Y. C. Cheng and W. H. Prusoff (Biochem. Pharmacol. 22, 3099–3102 (1973)).

Opioid Receptor Binding Studies

The μ-, δ- and κ-opioid receptor affinities of all new analogs were determined in binding assays based on displacement of μ-, δ- and κ-selective radioligands from rat brain membrane binding sites in the case of κ-ligands guinea pig brain homogenates were used, since the relative proportion of κ-binding sites is higher in guinea pig brain than in rat brain. The experimental procedure being used in our laboratory represents a modified version of the binding assay described by Pasternak et al. (Mol. Pharmacol. 11, 340–351, (1975)). Male Sprague-Dawley rats (300–350 g) from the Canadian Breeding Laboratories were decapitated and after removal of the cerebellum the brains were homogenized in 30 volumes of ice-cold standard buffer (50 mM Tris-HCl, pH 7.7). After centrifugation at 30,000 x g for 30 min at 4° C. the membranes were reconstituted in the original volume of standard buffer and incubated for 30 min at 37° C. (to realease bound endogenous ligands). Subsequent centrifugation and resuspension of the pellet in the initial volume of fresh standard buffer yielded the final membrane suspension. Aliquots (2 ml) of the membrane preparations were incubated for 1–2 h at 25° C. with 1 ml standard buffer containing the peptide to be tested and one of the following radioligands at the final concentration indicated: [$^3$H] DAMGO, μ-selective, 0.7 nM; [$^3$H]DSLET, [$^3$H]DPDPE, or [$^3$H]TIPP, δ-selective, 1.0 nM; and [$^3$H]69,563, κ-selective, 0.5 nM. The incubation was terminated by filtration through Whatman GF/B filters under vacuum at 4° C. Following two washings with 5 ml portions of ice-cold standard buffer the filters were transferred to scintillation vials and treated with 1 ml Protosol (New England Nuclear) for 30 min prior to the addition of 0.5 ml acetic acid and 10 ml Aquasol (New England Nuclear). After shaking for 30 min the vials were counted at an efficiency of 40–45%. All experiments were performed in duplicate and repeated at least three times. Specific binding of each of the three radioligands was defined by performing incubations in the presence of cold DAMGO, DSLET and U69,563, respectively, at a concentration of 1 micromolar. Values of half-maximal inhibition (IC50) of specific binding were obtained graphically from semilogarithmic plots. From the measured IC50-values, binding inhibition constants ($K_i$) were then calculated based on Cheng and Prusoff's equation (Biochem. Pharmcol. 22, 3099–3102 (1973)). Ratios of the $K_i$-values in the μ-, δ- and κ-representative binding assays are a measure of the receptor selectivety of the compound under investigation (e.g. $K_i^\mu/K_i^\delta$ indicates the selectivity for δ-receptors versus μ-receptors). None of the compounds according to the claimed invention had significant affinity for κ-receptors.

Potential Use

The δ antagonists may be used in combination with analgesics of the μ agonist type (e.g. morphine) to prevent the development of tolerance and dependence, as suggested by the results of E. E. Abdelhamid et at., J. Parmacol. Exp. Ther. 258, 299–303 (1991).

The δ antagonists according to the invention may also be therapeutically useful as immunosuppressive agents. Immunosuppressive effects of the less δ-selective and less "pure"δ antagonist naltrindole have been described by K. Arakawa et al. Transplantation Proc. 24, 696–697 (1992); Transplantation 53, 951–953 (1992).

Abbreviations

Aib=α-aminoisobutyric acid
Boc=tert-butoxycarbonyl
Cha=cyclohexylalanine
DAMGO=H-Tyr-D-Ala-Gly-Phe($N^\alpha$Me)-Gly-ol
DCC=dicyclohexylcarbodiimide
DIEA=diisopropylethylamine
Dmt=2',6'-dimethyltyrosine
DPDPE=[D-Pen$^2$,D-Pens$^5$]enkephalin
DSLET=H-Tyr-D-Ser-Gly-Phe-Leu-Thr-OH
FAB-MS=fast atom bombardment mass spectrometry
GPI=guinea pig ileum
HOBt=1-hydroxybenzotriazole
MVD=mouse vas deferens
Tic=1,2,3,4-tetrahydroisoquinoline-3-carboxylic acid
TIPP=H-Tyr-Tic-Phe-Phe-OH
U69,593=(5α, 7α, 8β)-(−)-N-methyl-[7-(1-pyrrolidinyl)-1-oxaspiro[4,5]dec-8-yl]benzeneacetamide

---

I claim:

1. A compound having the chemical structure of formula (I):

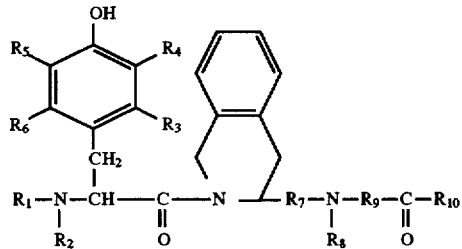

wherein:

$R_1$ is selected from the group consisting of H; $CH_3(CH_2)_n$ wherein n=0–12;

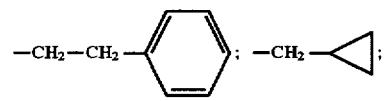

—$CH_2$—$CH$=$CH_2$; and arginine;

$R_2$ is selected from the group consisting of H; $CH_3(CH_2)_n$— wherein n=0–12; $CH_3$—;

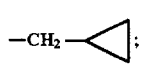

and

—$CH_2$—$CH$=$CH_2$ $R_3$, $R_4$, $R_5$ and $R_6$ are all H; or $R_4$ and $R_5$ are both H and $R_3$ and $R_6$ is each a $C_1$–$C_6$ alkyl group; or $R_3$, $R_5$ and $R_6$ are all H and $R_4$ is selected from the group consisting of F; Cl; Br; I; OH; $NH_2$; and $NO_2$;

$R_7$ is C=O or $CH_2$;

$R_8$ is H or a $C_1$–$C_6$ alkyl group;

$R_9$ is selected from the group consisting of

wherein m is 0–12;

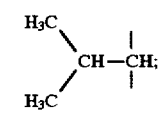

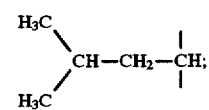

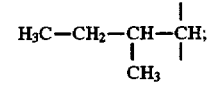

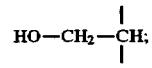

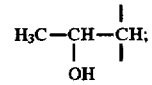

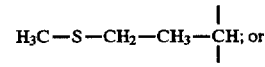

-continued

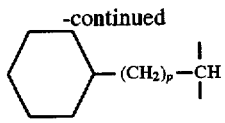

wherein p is 0–4;

R$_{10}$ is selected from the group consisting of OH; NH$_2$; and

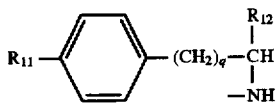

wherein R$_{11}$ is selected from the group consisting of H; NO$_2$; F; Cl; Br and I;

q is 0–3;

R$_{12}$ is selected from the group consisting of COOH; CONH$_2$; CH$_2$OH; or any additional amino acid; or R$_{10}$ is

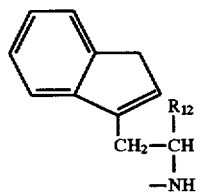

wherein

R$_{12}$ is as defined above with the proviso that said compound is neither H-Tyr-Tic-Ala-OH nor Tyr-L-Tic-Ala-NH$_2$.

2. The compound of claim 1, wherein

R$_1$ is either H or CH$_3$;
R$_2$ is either H or CH$_3$;
R$_3$ is either H or CH$_3$;
R$_4$ is H;
R$_5$ is H;
R$_6$ is either H or CH$_3$;
R$_7$ is either CO or CH$_2$;
R$_8$ is either H or CH$_3$;
R$_9$ is either

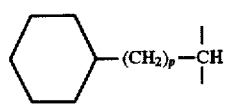

wherein p=0–4 or

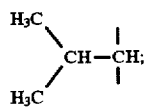

R$_{10}$ is

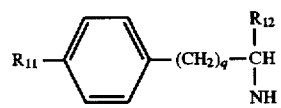

wherein R$_{11}$ is selected from the group consisting of H; NO$_2$; F; Cl; Br; and I;

q is 1–3; and

R$_{12}$ is COOH.

3. The compound according to claim 1, wherein

R$_1$ is either H or CH$_3$;
R$_2$ is either H or CH$_3$;
R$_2$ is CH$_3$;
R$_3$ is CH$_3$;
R$_4$ is H;
R$_5$ is H;
R$_6$ is CH$_3$;
R$_7$ is CH$_2$;
R$_8$ is either H or CH$_3$;
R$_9$ is

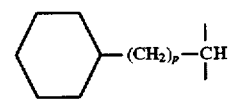

wherein p=0–4;

R$_{10}$ is

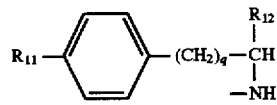

wherein R$_{11}$ is H, q is 1, and R$_{12}$ is COOH.

4. The compound of claim 1, wherein R$_7$ is CH$_2$.

5. The compound of claim 1, wherein R$_4$ and R$_5$ are hydrogen and R$_3$ and R$_6$ are both methyl groups.

6. The compound of claim 1, wherein R$_9$ is

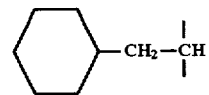

7. The compound of claim 1, wherein said compound is selected from the group consisting of:

H-Tyr-Tic-Cha-Phe-OH; SEQ ID NO:1
H-Tyr-TicΨ[CH$_2$-NH]Cha-Phe-OH; SEQ ID NO:2
H-Tyr-Tic-Cha-Phe-NH$_2$; SEQ ID NO:3
H-Tyr-Tic-Leu-Phe-OH; SEQ ID NO:4
H-Tyr-Tic-Val-Phe-OH; SEQ ID NO:5
H-Tyr-Tic-Nva-Phe-OH; SEQ ID NO:6
H-Tyr-Tic-Nle-Phe-OH; SEQ ID NO:7
H-Tyr-Tic-Ile-Phe-OH; SEQ ID NO:8
H-Tyr-Tic-Thr-Phe-OH; SEQ ID NO:9
H-Tyr-Tic-Met-Phe-OH; SEQ ID NO:10
H-Dmt-Tic-Cha-Phe-OH; SEQ ID NO:11
H-D-Dmt-Tic-Cha-Phe-OH; SEQ ID NO:12
H-Dmt-Tic-Cha-Phe-NH$_2$; SEQ ID NO:13

H-Tyr(3-I)-Tic-Cha-Phe-OH; SEQ ID NO:14

H-Dmt-TicΨ[CH$_2$—NH]Cha-Phe-OH; SEQ ID NO:15.

8. The compound of claim 7, wherein said compound is selected from the group consisting of:

H-Tyr-Tic-Cha-Phe-OH; SEQ ID NO:1

H-Tyr-TicΨ[CH$_2$—NH]Cha-Phe-OH; SEQ ID NO:2

H-Tyr-Tic-Val-Phe-OH; SEQ ID NO:5

H-Dmt-Tic-Cha-Phe-OH; SEQ ID NO:11

H-D-Dmt-Tic-Cha-Phe-OH; SEQ ID NO:12 and

H-Dmt-TicΨ[CH$_2$—NH]Cha-Phe-OH SEQ ID NO:15.

9. A method for preparing peptides of formula I of claim 1 by means of solid-phase synthesis wherein the coupling step in which a protected amino acid is added to the growing peptide chain is performed in an inert solvent using a coupling reagent.

10. The method of claim 9, wherein said inert solvent is selected from the group containing CH$_2$Cl$_2$, DMF; and a mixture of CH$_2$CL$_2$/DMF(3:1 v/v); and wherein the coupling agent is selected from the group consisting of N,N'-dicyclohexylcarbodiimide/1-hydroxybenzotriazole; N,N'-diisopropylcarbodiimide/1-hydroxybenzotriazole; and benzotria-zolyloxytris-(dimethylamino)phosphonium hexafluorophosphate.

11. The method of claim 10, further comprising a) attaching Boc-Tic-OH to a dipeptide immobilized on a resin;

b) attaching Boc-Tyr(Boc)-OH to a peptide linked to said resin.

12. The method of claim 9 wherein Boc-Tic aldehyde is added to said growing peptide chain and a reductive alkylation reaction between said Boc-Tic aldehyde and the amino group of the last amino acid in said growing peptide chain is then performed using sodium cyanoborohydride in acidified DMF.

13. A pharmaceutical preparation comprising, in admixture with one or more pharmaceutical carriers, the compound of claim 1.

14. A method for the treatment of a subject suffering from pain, comprising administering the compound of claim 1, to said subject in an amount sufficient to reduce or eliminate said pain.

15. A method for producing immunosuppression in a patient, comprising administering the compound of claim 1 to said subject in an amount sufficient to produce said immunosuppression.

* * * * *

SEQUENCE LISTING ( 1 ) GENERAL INFORMATION:

( i i i ) NUMBER OF SEQUENCES: 15

( 2 ) INFORMATION FOR SEQ ID NO: 1:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: N-terminal ( i x ) FEATURE:
        ( A ) NAME/KEY: Modified-site
        ( B ) LOCATION: 2
        ( D ) OTHER INFORMATION: /label=X
            / note=
            " X=Tic=1,2,3,4-tetrahydroisoquinoline-3-carboxylic acid"

( i x ) FEATURE:
        ( A ) NAME/KEY: Modified-site
        ( B ) LOCATION: 3
        ( D ) OTHER INFORMATION: /label=X
            / note= "X=Cha=cyclohexylalanine"

( x i ) SEQUENCE DESCRIPTION: SEQ ID NO: 1:

Tyr Xaa Xaa Phe
    1

( 2 ) INFORMATION FOR SEQ ID NO: 2:

( i ) SEQUENCE CHARACTERISTICS:

(A) LENGTH: 4 amino acids
                (B) TYPE: amino acid
                (D) TOPOLOGY: linear (ii) MOLECULE TYPE: peptide (v) FRAGMENT TYPE: N-terminal (ix) FEATURE:
                (A) NAME/KEY: Modified-site
                (B) LOCATION: 2
                (D) OTHER INFORMATION: /label=X
                    / note= "X=Tic(psi)[CH2-NH];
                    Tic=1,2,3,4-tetrahydroisoquinoline-3-carboxylic
                    acid"

(ix) FEATURE:
                (A) NAME/KEY: Modified-site
                (B) LOCATION: 3
                (D) OTHER INFORMATION: /label=X
                    / note= "X=Cha=cyclohexylalanine"

(xi) SEQUENCE DESCRIPTION: SEQ ID NO: 2:

Tyr  Xaa  Xaa  Phe
    1

(2) INFORMATION FOR SEQ ID NO: 3:

(i) SEQUENCE CHARACTERISTICS:
                (A) LENGTH: 4 amino acids
                (B) TYPE: amino acid
                (D) TOPOLOGY: linear (ii) MOLECULE TYPE: peptide (v) FRAGMENT TYPE: N-terminal (ix) FEATURE:
                (A) NAME/KEY: Modified-site
                (B) LOCATION: 2
                (D) OTHER INFORMATION: /label=X
                    / note=
                    " X=Tic=1,2,3,4-tetrahydroisoquinoline-3-carboxylic
                    acid"

(ix) FEATURE:
                (A) NAME/KEY: Peptide
                (B) LOCATION: 3
                (D) OTHER INFORMATION: /label=X
                    / note= "X=Cha=cyclohexylalanine"

(xi) SEQUENCE DESCRIPTION: SEQ ID NO: 3:

Tyr  Xaa  Xaa  Phe
    1

(2) INFORMATION FOR SEQ ID NO: 4:

(i) SEQUENCE CHARACTERISTICS:
                (A) LENGTH: 4 amino acids
                (B) TYPE: amino acid
                (D) TOPOLOGY: linear (ii) MOLECULE TYPE: peptide (v) FRAGMENT TYPE: N-terminal (ix) FEATURE:
                (A) NAME/KEY: Modified-site
                (B) LOCATION: 2
                (D) OTHER INFORMATION: /label=X
                    / note=
                    " X=Tic=1,2,3,4-tetrahydroisoquinoline-3-carboxylic
                    acid"

(xi) SEQUENCE DESCRIPTION: SEQ ID NO: 4:

Tyr Xaa Leu Phe
    1

( 2 ) INFORMATION FOR SEQ ID NO: 5:

( i ) SEQUENCE CHARACTERISTICS:
            ( A ) LENGTH: 4 amino acids
            ( B ) TYPE: amino acid
            ( D ) TOPOLOGY: linear ( i i ) MOLECULE TYPE: peptide ( v ) FRAGMENT TYPE: N-terminal ( i x ) FEATURE:
            ( A ) NAME/KEY: Modified-site
            ( B ) LOCATION: 2
            ( D ) OTHER INFORMATION: /label=X
                    / note=
                    " X=Tic=1,2,3,4-tetrahydroisoquinoline-3-carboxylic
                    acid"

( x i ) SEQUENCE DESCRIPTION: SEQ ID NO: 5:

Tyr Xaa Val Phe
    1

( 2 ) INFORMATION FOR SEQ ID NO: 6:

( i ) SEQUENCE CHARACTERISTICS:
            ( A ) LENGTH: 4 amino acids
            ( B ) TYPE: amino acid
            ( D ) TOPOLOGY: linear ( i i ) MOLECULE TYPE: peptide ( v ) FRAGMENT TYPE: N-terminal ( i x ) FEATURE:
            ( A ) NAME/KEY: Modified-site
            ( B ) LOCATION: 2
            ( D ) OTHER INFORMATION: /label=x
                    / note=
                    " X=Tic=1,2,3,4-tetrahydroisoquinoline-3-carboxylic
                    acid"

( i x ) FEATURE:
            ( A ) NAME/KEY: Modified-site
            ( B ) LOCATION: 3
            ( D ) OTHER INFORMATION: /label=X
                    / note= "X=Nva=norvaline"

( x i ) SEQUENCE DESCRIPTION: SEQ ID NO: 6:

Tyr Xaa Xaa Phe
    1

( 2 ) INFORMATION FOR SEQ ID NO: 7:

( i ) SEQUENCE CHARACTERISTICS:
            ( A ) LENGTH: 4 amino acids
            ( B ) TYPE: amino acid
            ( D ) TOPOLOGY: linear ( i i ) MOLECULE TYPE: peptide ( v ) FRAGMENT TYPE: N-terminal ( i x ) FEATURE:
            ( A ) NAME/KEY: Modified-site
            ( B ) LOCATION: 2
            ( D ) OTHER INFORMATION: /label=x
                    / note=
                    " X=1,2,3,4-tetrahydroisoquinoline-3-carboxylic
                    acid"

( i x ) FEATURE:

(A) NAME/KEY: Modified-site
        (B) LOCATION: 3
        (D) OTHER INFORMATION: /label=X
                / note= "X=norleucine"

(xi) SEQUENCE DESCRIPTION: SEQ ID NO: 7:

Tyr  Xaa  Xaa  Phe
    1

(2) INFORMATION FOR SEQ ID NO: 8:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (v) FRAGMENT TYPE: N-terminal (ix) FEATURE:
        (A) NAME/KEY: Modified-site
        (B) LOCATION: 2
        (D) OTHER INFORMATION: /label=X
                / note=
                " X=Tic=1,2,3,4-tetrahydroisoquinoline-3-carboxylic
                acid"

(xi) SEQUENCE DESCRIPTION: SEQ ID NO: 8:

Tyr  Xaa  Ile  Phe
    1

(2) INFORMATION FOR SEQ ID NO: 9:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (v) FRAGMENT TYPE: N-terminal (ix) FEATURE:
        (A) NAME/KEY: Modified-site
        (B) LOCATION: 2
        (D) OTHER INFORMATION: /label=X
                / note=
                " X=Tic=1,2,3,4-tetrahydroisoquinoline-3-carboxylic
                acid"

(xi) SEQUENCE DESCRIPTION: SEQ ID NO: 9:

Tyr  Xaa  Thr  Phe
    1

(2) INFORMATION FOR SEQ ID NO: 10:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (v) FRAGMENT TYPE: N-terminal (ix) FEATURE:
        (A) NAME/KEY: Modified-site
        (B) LOCATION: 2
        (D) OTHER INFORMATION: /label=X
                / note=
                " X=Tic=1,2,3,4-tetrahydroisoquinoline-3-carboxylic
                acid"

( x i ) SEQUENCE DESCRIPTION: SEQ ID NO: 10:

Tyr Xaa Met Phe
1

( 2 ) INFORMATION FOR SEQ ID NO: 11:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: N-terminal ( i x ) FEATURE:
        ( A ) NAME/KEY: Modified-site
        ( B ) LOCATION: 1
        ( D ) OTHER INFORMATION: /label=X
            / note= "X=Dmt=2',6'-dimethyltyrosine"

( i x ) FEATURE:
        ( A ) NAME/KEY: Modified-site
        ( B ) LOCATION: 2
        ( D ) OTHER INFORMATION: /label=X
            / note=
            " X=Tic=1,2,3,4-tetrahydroisoquionoline-3-carboxyl
            ic acid"

( i x ) FEATURE:
        ( A ) NAME/KEY: Modified-site
        ( B ) LOCATION: 3
        ( D ) OTHER INFORMATION: /label=X
            / note= "X=Cha=cyclohexylalanine"

( x i ) SEQUENCE DESCRIPTION: SEQ ID NO: 11:

Xaa Xaa Xaa Phe
1

( 2 ) INFORMATION FOR SEQ ID NO: 12:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: N-terminal ( i x ) FEATURE:
        ( A ) NAME/KEY: Modified-site
        ( B ) LOCATION: 1
        ( D ) OTHER INFORMATION: /label=X
            / note= "X=D-Dmt; Dmt=2',6'-dimethyltyrosine"

( i x ) FEATURE:
        ( A ) NAME/KEY: Modified-site
        ( B ) LOCATION: 2
        ( D ) OTHER INFORMATION: /label=X
            / note=
            " X=Tic=1,2,3,4-tetrahydroisoquinoline-3-carboxylic
            acid"

( i x ) FEATURE:
        ( A ) NAME/KEY: Modified-site
        ( B ) LOCATION: 3
        ( D ) OTHER INFORMATION: /label=X
            / note= "X=Cha=cyclohexylalanine"

( x i ) SEQUENCE DESCRIPTION: SEQ ID NO: 12:

Xaa Xaa Xaa Phe
1

( 2 ) INFORMATION FOR SEQ ID NO: 13:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: N-terminal ( i x ) FEATURE:
        ( A ) NAME/KEY: Modified-site
        ( B ) LOCATION: 1
        ( D ) OTHER INFORMATION: /label=X
            / note= "X=Dmt=2',6'-dimethyltyrosine"

( i x ) FEATURE:
        ( A ) NAME/KEY: Modified-site
        ( B ) LOCATION: 2
        ( D ) OTHER INFORMATION: /label=X
            / note=
            " X=Tic=1,2,3,4-tetrahydroisoquinoline-3-carboxylic
            acid"

( i x ) FEATURE:
        ( A ) NAME/KEY: Modified-site
        ( B ) LOCATION: 3
        ( D ) OTHER INFORMATION: /label=x
            / note= "X=Cha=cyclohexylalanine"

( x i ) SEQUENCE DESCRIPTION: SEQ ID NO: 13:

Xaa Xaa Xaa Phe
1

( 2 ) INFORMATION FOR SEQ ID NO: 14:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: N-terminal ( i x ) FEATURE:
        ( A ) NAME/KEY: Modified-site
        ( B ) LOCATION: 1
        ( D ) OTHER INFORMATION: /label=X
            / note= "X=Tyr(3'-I)"

( i x ) FEATURE:
        ( A ) NAME/KEY: Modified-site
        ( B ) LOCATION: 2
        ( D ) OTHER INFORMATION: /label=X
            / note=
            " X=Tic=1,2,3,4-tetrahydroisoquinoline-3-carboxylic
            acid"

( i x ) FEATURE:
        ( A ) NAME/KEY: Modified-site
        ( B ) LOCATION: 3
        ( D ) OTHER INFORMATION: /label=X
            / note= "X=Cha=cyclohexylalanine"

( x i ) SEQUENCE DESCRIPTION: SEQ ID NO: 14:

Xaa Xaa Xaa Phe
1

( 2 ) INFORMATION FOR SEQ ID NO: 15:

( i ) SEQUENCE CHARACTERISTICS:
        ( A ) LENGTH: 4 amino acids
        ( B ) TYPE: amino acid
        ( D ) TOPOLOGY: linear -continued

```
    (  i  i  ) MOLECULE TYPE: peptide (  v  ) FRAGMENT TYPE: N-terminal (  i  x  ) FEATURE:
             ( A ) NAME/KEY: Modified-site
             ( B ) LOCATION: 1
             ( D ) OTHER INFORMATION: /label=X
                     / note= "X=Dmt=2',6'-dimethyltyrosine"

(  i  x  ) FEATURE:
             ( A ) NAME/KEY: Modified-site
             ( B ) LOCATION: 2
             ( D ) OTHER INFORMATION: /label=X
                     / note= "X=Tic(psi)[CH2-NH];
                       Tic=1,2,3,4-tetrahydroisoquinoline-3-carboxylic
                       acid"

(  i  x  ) FEATURE:
             ( A ) NAME/KEY: Modified-site
             ( B ) LOCATION: 3
             ( D ) OTHER INFORMATION: /label=X
                     / note= "X=Cha=cyclohexylalanine"

(  x  i  ) SEQUENCE DESCRIPTION: SEQ ID NO: 15:

Xaa  Xaa  Xaa  Phe
    1
```